(12) United States Patent
Lubiene et al.

(10) Patent No.: US 10,023,856 B2
(45) Date of Patent: Jul. 17, 2018

(54) ENZYME COMPOSITION FOR DNA END REPAIR, ADENYLATION, PHOSPHORYLATION

(71) Applicant: Thermo Fisher Scientific Baltics UAB, Vilnius (LT)

(72) Inventors: Judita Lubiene, Vilnius (LT); Arturas Berezniakovas, Vilnius (LT); Arvydas Lubys, Vilnius (LT)

(73) Assignee: Thermo Fisher Scientific Baltics UAB, Vilnius (LT)

( * ) Notice: Subject to any disclaimer, the term of this patent is extended or adjusted under 35 U.S.C. 154(b) by 213 days.

(21) Appl. No.: 14/494,684

(22) Filed: Sep. 24, 2014

(65) Prior Publication Data

US 2015/0087557 A1  Mar. 26, 2015

Related U.S. Application Data

(60) Provisional application No. 61/904,543, filed on Nov. 15, 2013, provisional application No. 61/882,480, filed on Sep. 25, 2013.

(51) Int. Cl.
| | |
|---|---|
| *C12N 9/12* | (2006.01) |
| *C12N 11/18* | (2006.01) |
| *C12N 9/96* | (2006.01) |
| *C12N 9/22* | (2006.01) |

(52) U.S. Cl.
CPC ............. *C12N 9/96* (2013.01); *C12N 9/1205* (2013.01); *C12N 9/1241* (2013.01); *C12N 9/1252* (2013.01); *C12N 9/22* (2013.01); *C12N 11/18* (2013.01); *C12Y 207/01078* (2013.01)

(58) Field of Classification Search
None
See application file for complete search history.

(56) References Cited

U.S. PATENT DOCUMENTS

| | | |
|---|---|---|
| 9,267,130 B2 | 2/2016 | Martin et al. |
| 2003/0138805 A1* | 7/2003 | Loffert .................. C12P 19/34 435/6.18 |
| 2004/0002076 A1* | 1/2004 | Wang .................. C07K 14/195 435/6.11 |
| 2011/0086406 A1 | 4/2011 | Martin et al. |
| 2014/0228256 A1 | 8/2014 | Zhang et al. |

OTHER PUBLICATIONS

Brenda. EC 2.7.7.7 & EC 2.7.1.78. retrieved from http://www.brenda-enzymes.org/index.php on Jul. 24, 2017.*
Mena. Extended Stability of Taq DNA Polymerase and T4 DNA Ligase at Various TemperaturesBioTechniques 34:264-268. Feb. 2003.*
Lucigen, NxSeq® DNA Sample Prep Kits, http://lucigen.com/store/NxSeq-DNA-Sample-Prep-Kits?printable=Y (2013).
New England BioLabs, NEBNext® Ultra™ DNA Library Prep Kit for Illumine®, https://www.neb.com/products/e7370-nebnext-ultra-dna-library-prep-kit-for-illumina (2013).
NuGen, Ovation® Ultralow Library Systems, http://www.nugeninc.com/nugen/index.cfm/linkservid/016E2EEC-4950-4E3D-B6F615F955DD0CCF/showMeta/0/ (2010).
EMD Millipore, Novagen® PureGenome™ High Efficiency Next Generation Sequencing (NGS) Library Preparation Reagents, http://www.emdmillipore.com/chemicals/en_CA/Merck-US-Site/USD/ViewProductDocuments-File?ProductSKU=EMD_BIOPGN001&DocumentType=USP&DocumentId=%2Femd%2Fbiosciences%2Fuserprotocols%2Fen-US%2FTB574.pdf&DocumentSource=GDS (2012).
Adessi et al. Solid phase DNA amplification: characterisation of primer attachment and amplification mechanisms. Nucleic Acids Research 28 (2000) e87, 8 pages.
Cheung and Nelson. Whole genome amplification using a degenerate oligonucleotide primer allows hundreds of genotypes to be performed on less than one nanogram of genomic DNA. Pro. Nat. Acad. Sci. USA 93 (1996) 14676-14679.
Margulies et al. Genome sequencing in microfabricated high-density picolitre reactors. Nature 437 (2005) 376-380.
Mitra and Church. In situ localized amplification and contact replication of many individual DNA molecules. Nucleic Acids Research 27 (1999) e34, 6 pages.
Shendure et al. Accurate Multiplex Polony Sequencing of an Evolved Bacterial Genome. Science 309 (2005) 1728-1732.
International Search Report PCT/EP2014/070478, dated Dec. 16, 2014, 5 pages.
Written Opinion of the International Searching Authority PCT/EP2014/070478, dated Dec. 16, 2014, 6 pages.
New England BioLabs Inc. Library Preparation—NEBnext Ultra DNA Library Prep Kit for Illumina, Feb. 2013 (Feb. 2012), XP055156837, Retrieved from the Internet: URL:https://www.neb.com/~/media/Catalog/A11-Products/23EF8BC783C74-9D9B664D90C8C72FA73/Datacards or Manual s /manua l E7370.pdf.
Lucigen Corporation. NxSeq DNA Sample Prep Kit, Aug. 2013 (Aug. 2013), XP055156845, Retrieved from the Internet: URL:http://lucigen.com/docs/manuals/MA134-NxSeq-DNA-Prep-Kit.pdf.
PureGenome™. High Efficiency Next Generation Sequencing (NGS) Library Preparation Reagents, Jan. 1, 2012, No. TB574 Rev. A 0812 JN, Jan. 1, 2012 (Jan. 1, 2012), p. 7 pp. XP007922930.
Kawata et al., "Preparation of a Genomic Library Using a Ta Vector," Preparative Biochemistry and Biotechnology, 1999, 29(1):91-100.
Agback et al., "Architecture of Nonspecific Protein-DNA Interactions in the Sso7d-DNA Complex," Nature Structural Biology, 1998, 5(7): 579-584.

(Continued)

*Primary Examiner* — Yong D Pak
(74) *Attorney, Agent, or Firm* — McNeill Baur PLLC

(57) ABSTRACT

Enzyme compositions and their method of use that provide ready-to-use master mixtures. The compositions comprise a modified thermophilic DNA polymerase lacking 5'-3' and 3'-5' exonuclease activity premixed with T4 DNA polymerase, Klenow fragment and T4 polynucleotide kinase and all other necessary components, including reaction buffer and nucleoside triphosphates, required to perform DNA blunting, phosphorylation, and single nucleotide extension reactions in one tube and in two steps. Among other benefits, the mixture of different enzymes, buffers and nucleoside triphosphates is stable during prolonged storage.

13 Claims, 7 Drawing Sheets

(56) References Cited

OTHER PUBLICATIONS

Davidson et al., "Insertion of the T3 DNA Polymerase Thioredoxin Binding Domain Enhances the Processivity and Fidelity of Taq DNA Polymerase," Nucleic Acids Research, 2003, 31(16):4702-4709.
Hopfner et al., "Crystal Structure of a Thermostable Type B DNA Polymerase from *Thermoscoccus gorgonarius*," PNAS, 1999, 96:3600-3605.
Suzuki et al., "Thermus Aquaticus DNA Polymerase I Mutants with Altered Fidelity," Journal of Biological Chemistry, 2000, 275(42):32728-32735.
Vielle et al., "Hyperthermophilic Enzymes: Sources, Uses and Molecular Mechanisms for Thermostability," Microbiology and Molecular Biology Reviews, 2001, 65(1):1-43.

\* cited by examiner

FIG. 1

| Oligo-duplex | | Primers | |
|---|---|---|---|
| G-38 | 5' | Cy-5-TGCAGACATGGGTAGGCATCCTTGGCGTAGTTACCAAG (SEQ ID NO: 1) | 3' |
| | 3' | ACGTCTGTACCCATCCGTAGGAACCGCATCAATGGTTC (SEQ ID NO: 2) | 5' |
| C-35 | 5' | Cy-5-TGCAGACATGGGTAGGCATCCTTGGCGTAGTTACC (SEQ ID NO: 3) | 3' |
| | 3' | ACGTCTGTACCCATCCGTAGGAACCGCATCAATGG (SEQ ID NO: 4) | 5' |
| T-32 | 5' | Cy-5-TGCAGACATGGGTAGGCATCCTTGGCGTAGTT (SEQ ID NO: 5) | 3' |
| | 3' | ACGTCTGTACCCATCCGTAGGAACCGCATCAA (SEQ ID NO: 6) | 5' |
| A-29 | 5' | Cy-5-TGCAGACATGGGTAGGCATCCTTGGCGTA (SEQ ID NO: 7) | 3' |
| | 3' | ACGTCTGTACCCATCCGTAGGAACCGCAT (SEQ ID NO: 8) | 5' |

ENZYME COMPOSITION FOR DNA END REPAIR, ADENYLATION, PHOSPHORYLATION

This applications claims priority to U.S. patent application Ser. Nos. 61/882,480 filed Sep. 25, 2013, and 61/904,543 filed Nov. 15, 2013, each of which is incorporated by reference herein in its entirety.

Several methods for high throughput DNA sequencing (Nature. 437, 376-380 (2005); Science. 309 (2005) 728-1732) rely on a universal amplification reaction, whereby a DNA sample is randomly fragmented, then is treated such that the ends of the different fragments all contain the same DNA sequence. Fragments with universal ends can be amplified in a single reaction with a single pair of amplification primers. Separation of the library of fragments to the single molecule level prior to amplification ensures that the amplified molecules form discrete populations. These discrete populations can then be further analyzed. Such separations can be performed either in emulsions (Nature. 437, 376-380 (2005); Science. 309, 5741, 1728-1732 (2005)), or on a surface (Nucleic Acids Research 27, e34 (1999); Nucleic Acids Research 28, e87 (2000)).

Adding universal priming sequences onto the ends of targets to be amplified by the polymerase chain reaction (PCR) can be achieved by a variety of methods known to those skilled in the art. For example, a universal primer containing a universal sequence at its 5' end and a degenerate sequence at its 3' end can be used in PCR (DOP-PCR, e.g., PNAS 93 (1996) 14676-14679) to amplify fragments randomly from a complex target sequence or a complex mixture of target sequences. The degenerate 3' portion of the primer anneals at random DNA positions and can be extended to generate a copy of the target that has the universal sequence at its 5' end.

Alternatively, adaptors that contain universal priming sequences can be ligated onto the ends of the target sequences. The adaptors may be single-stranded or double-stranded. Double-stranded adaptors may have overhanging ends or may have blunt ends. Adaptors with overhanging ends are complementary to overhanging ends on the target sequences that may have been generated by digestion with a restriction endonuclease, or added with a DNA polymerase or terminal transferase. Adaptors with blunt ends are used with targets that are also blunt ended, formed during a process to shear the DNA into fragments, or formed by an end repair reaction as known to one skilled in the art.

A single adaptor or two different adaptors may be used in a ligation reaction with target sequences. If a target has been manipulated such that its ends are the same, i.e. both are blunt or both have the same overhang, then ligation of a single compatible adaptor will generate a template with that adaptor on both ends. However, if two compatible adaptors, adaptor A and adaptor B, are used, then three permutations of ligated products are formed: template with adaptor A on both ends, template with adaptor B on both ends, and template with adaptor A on one end and adaptor B on the other end. This last product is, under some circumstances, the only desired product from the ligation reaction and consequently additional purification steps are necessary following the ligation reaction to purify it from the ligation products that have the same adaptor at both ends.

Many molecular biology research techniques and applications, such as preparing DNA libraries for Next Generation Sequencing (NGS) require adding synthetic DNA adapters to both ends of DNA fragments of interest. Synthetic adaptors are usually added by the following steps: (1) a DNA sample of interest is physically or enzymatically sheared, (2) the resulting DNA fragments are blunted and phosphorylated, (3) the 3' ends of the blunted DNA fragments are extended by one nucleotide, preferentially by dATP, (4) the resulting DNA fragments are ligated to adapters that have dTTP extensions at their 3'-end. dA-tailing of target DNA fragments prevents them from intra- or intermolecular ligation with other DNA fragments and thus increases the yield of fragments of the expected structure.

It was recently realized that both end repair/blunting and dA-tailing reactions of DNA fragments could be done in one tube, first by performing DNA blunting and phosphorylation reactions at a lower temperature, and then tailing of the blunted DNA fragments at a higher temperature. Commercial NGS sample preparation kits that work in a similar way are available (NxSeq DNA Sample Prep Kit, Lucigen; NEBNext Ultra DNA Library Prep Kit, Illumina from NEB; PureGenome HE NGS Library Prep Reagents, EMD Milipore). However, only EMD Millipore discloses the enzyme used for DNA 3' end terminal extension: the thermophilic NovaTaq DNA polymerase. The other two suppliers provide product use recommendations (incubation at 65-72° C.) that lead one skilled in the art to believe that thermophilic DNA polymerases are also used for the dA tailing step. Table 1 shows commercial reagents and protocols of DNA end repair and dA-tailing reactions from New England Biolabs, EMD Milipore, and Lucigen.

TABLE 1

One-tube DNA end repair and dA-tailing conditions and reagents used from commercial suppliers' kits.

| | NEB NEBNext Ultra DNA library Prep Kit for illumine | Lucigen NxSeq DNA Sample Prep kit | EMD Milipore PureGenome HE NGS library Prep Reagents |
|---|---|---|---|
| Reagents for DNA end repair and dA-tailing reactions | End Repair Reaction Buffer End Prep Enzyme Mix | NxSeq Enzyme Buffer NxSeq Enzyme Mix | Conversion buffer 10 mM ATP 10 mM dNTP T4 DNA polymerase T4 PNK NovaTaq DNA polymerase |
| Reaction conditions | end repair - 30 min at 20° C., dA-tailing - 30 min at 65° C. | end repair - 20 min at 25° C., dA-tailing - 20 min at 72° C. | end repair - 20 min at 25° C., dA-tailing - 20 min at 72° C. |

NEB and Lucigen products represent reagent sets, where all enzymes needed for DNA end repair (blunting and phosphorylation) and dA-tailing reactions are combined by the user into a single mixture (enzyme cocktail). However, the reaction buffer is supplied separately and is not premixed with enzymes into a ready-to-use Master Mix. EMD Milipore kit includes all components of DNA end repair and dA-tailing reactions provided in separate vials. Other suppliers are proposing a two-component workflow where the DNA fragments of interest are first blunted and phosphorylated and then, after inactivation or removal of the first step enzymes, the dA-tailing enzyme is added.

Two well-characterized polymerases are generally recommended as preferred enzymes for the dA-tailing reaction used in many cloning protocols: either mesophilic Klenow fragment mutant which is deficient in 3'-5' exonuclease activity, or thermophilic Taq DNA polymerase. The capability of these enzymes to perform non-template directed synthesis, such as adding an extra nucleotide at DNA 3' end of a DNA fragment, is known to one skilled in the art.

However, both enzymes are known to exhibit certain preferences, the most important of which is that they favor 3'-terminal extension of DNA fragments possessing pyrimidines (dT or dC) at their 3' ends and only partial extension of those DNA fragments that have 3'-terminal purines (dA or dG). As a result, blunt DNA fragments remaining after inefficient dA-tailing reaction may participate in the intermolecular ligation reaction thereby forming hybrid DNA molecules that do not exist in genome in the native state. In case such hybrid molecules contain dA extension at their 3' ends adapter sequences may be added to them and such molecules may then proceed into sequencing reaction. If library preparation contains many such chimeric molecules they may later complicate or compromise genome sequence assembly. Chimeric DNA molecules in NGS applications may compromise the assembly of sequenced genomes. Thus, improved enzyme compositions for non-biased DNA fragment end repair/tailing for NGS library preparation applications are needed.

The disclosed enzyme compositions were stable during prolonged storage, and also exhibited better efficiency and less bias when compared with thermophilic Taq DNA polymerase and mesophilic Klenow fragment exo⁻ mutant conventionally used in dA-tailing step. The enzymes used for dA tailing reaction in the disclosed composition are chimeric DNA polymerases, which do not possess either 5'-3', or 3'-5' exonuclease activity, generated by fusion between *Thermus* sp. DNA polymerase and a nonspecific DNA binding domain. DNA binding domains suitable for generating such chimeric DNA polymerases used in the present invention may be selected from the group consisting of a DNA binding domains from a Sso family DNA binding proteins, including, without limitation, Sso7d basic chromosomal protein from the hyperthermophilic archaeabacteria *Sulfolobus solfataricus* and Sac7d protein from *S. acidocaldarius*. In one embodiment, the enzyme is *Thermus brockianus* DNA polymerase fused with a nonspecific DNA binding domain (mod-Tbr, exemplified by the enzymes used in Thermo Scientific DyNAmo™ products, deposit with Microbial Strain Collection of Latvia (MSCL, Accession No. P1397, Identification Reference BL21(DE3)(pRAT5-DIVOpt)) having no 5'-3' and 3'-5' exonuclease activity. In another embodiment the enzyme is *Thermus aquaticus* DNA polymerase fused with a non-specific DNA-binding domain (mod-Taq), deposit with MSCL (Accession No. P1396, Identification Reference ER2566(pLATE51-fusion9)), that does not possess either 5'-3', or 3'-5' exonuclease activity.

One embodiment is the disclosed enzyme compositions provided in ready-to-use master mixtures ("Master Mix"). The Master Mix contains mod-Tbr or mod-Taq premixed with T4 DNA polymerase, Klenow fragment, T4 polynucleotide kinase, and all other components including reaction buffer and nucleoside triphosphates, wherein dATP concentration is 10× higher than that of dGTP and 5× higher than that of dTTP and dCTP, required to perform DNA blunting, phosphorylation and dA tailing reactions in one tube, in a two-step reaction. Such a mixture of different enzymes, buffers and nucleoside triphosphates is stable during prolonged storage at −20° C. temperature.

BRIEF DESCRIPTION OF THE DRAWINGS

FIG. 1 shows double stranded oligos terminating in G, C, T, and A respectively used in Example 2.

Figure 2:
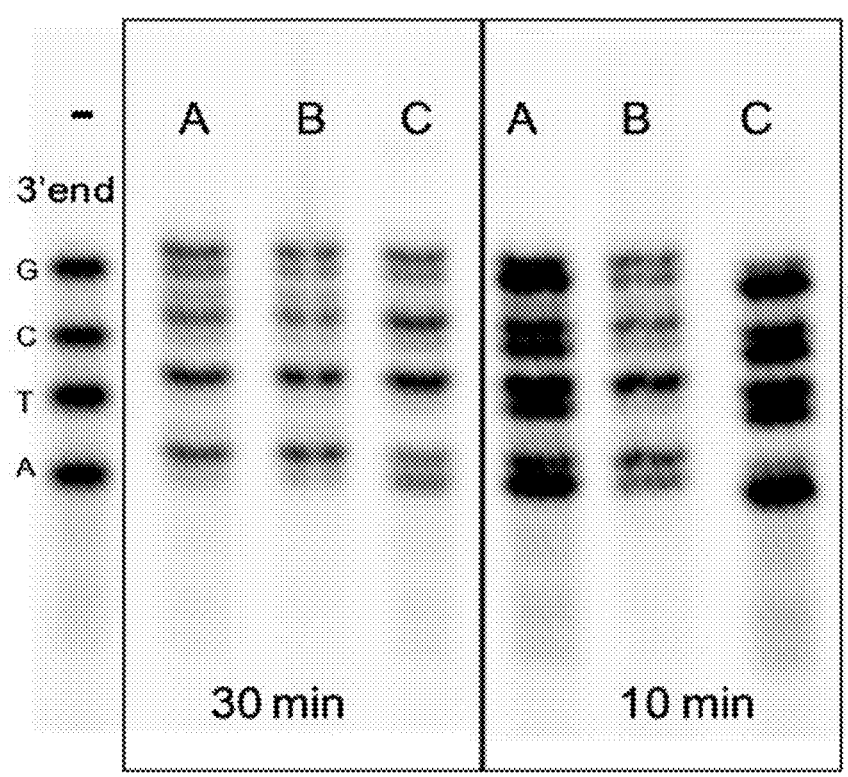
FIG. 2 shows separated duplex oligos of FIG. 1 treated with Klenow fragment exo⁻ in various reaction buffers showing dA-tailing efficiency.

In one embodiment, the disclosed composition comprises the following components:

Enzymes:
1 u/μl T4 polynucleotide kinase
0.32 u/μl T4 DNA polymerase
0.12 u/μl Klenow fragment
0.2 u/μl mod-Tbr DNA polymerase
Reaction co-factors and nucleotides:
20 mM MgCl$_2$
2 mM dATP
0.4 mM dCTP
0.4 mM dTTP
0.2 mM dGTP
2 mM ATP The composition ionic strength and pH may be formulated using 100 mM-105 mM Tris-HCl, pH 8.3 and monovalent metal hydrochloric acid salts, e.g. NaCl, KCl, LiCl, in a concentration range from 20 mM to 50 mM. In one embodiment, the composition contains the following stabilizers and cryoprotectants: 20 mM DTT, 0.2% Triton X-100, 12% (v/v) glycerol, 0.07% NP 40, 0.07% Tween 20, and 0.024 mM EDTA.

One embodiment is a method for DNA end-repair and terminal nucleotide addition in single container, such as Eppendorf type tubes, 96 well plates or any other vessels used for setting up enzymatic reactions. In one embodiment, DNA end-repair comprises generating blunt-ended and phosphorylated DNA fragments. In one embodiment, DNA fragments are mixed with the described composition in a single container, and DNA end-repair and nucleotide tailing of the DNA fragments is performed in the single container. In one embodiment, the terminal nucleotide is adenosine, which is added to the 3' terminal end of the DNA fragment, and referred to as dA tailing. In one embodiment, the contents of the single container are subjected to a first reaction condition to promote the DNA end-repair reaction, and then the contents of the container is subjected to a second reaction condition to promote the dA-tailing reaction and to inactivate the DNA end-repair reaction, where the DNA end-repair reaction comprises blunting and phosphorylating the DNA fragments, and the dA-tailing reaction comprises adenylation of the DNA fragments by adding a single dA to the 3' ends of the end-repaired DNA fragments. In one embodiment, the first reaction condition comprises subjecting the contents of the single container to a temperature ranging from 18° C. to 22° C. inclusive, for a period of time from 5 to 10 minutes inclusive, and the second reaction condition comprises subjecting the container contents to a temperature of 72° C. to 75° C. inclusive for a period of time from 10 to 20 minutes inclusive. In one embodiment, the first reaction condition comprises subjecting the container contents to a temperature of about 20° C. for about five minutes, and the second reaction condition comprises subjecting the container contents to a temperature of about 72° C. for about ten minutes. In one embodiment, the yield of dA-tailed DNA fragments exceeds 75%.

In one embodiment, the method further comprises generating DNA fragments prior to DNA end-repair. DNA fragments may be generated by physical DNA shearing methods such as ultrasound nebulization, and hydrodynamic shearing, or by enzymatic digestion using DNaseI or other endonucleases. In one embodiment, the DNA sample comprises genomic DNA. In one embodiment, the method may further comprise generating a DNA library by joining synthetic DNA adapters to either or both ends of the nucleotide tailed DNA fragment. In one embodiment, the method further comprises ligating the end-repaired and dA-tailed DNA fragments to synthetic DNA adapters possessing dT extensions at their 3' ends.

One embodiment is a kit containing the disclosed composition and instructions for performing the disclosed method for one-tube DNA blunting and dA tailing. In one embodiment the disclosed composition comprises 0.5 u/µl-1.5 u/µl T4 polynucleotide kinase, 0.2 u/µl-0.5 u/µl T4 DNA polymerase, 0.1 u/µl-0.2 Klenow fragment, and 0.1 u/µl-0.5 u/µl mod-Tbr DNA polymerase; reaction co-factors and nucleotides: 20 mM $MgCl_2$ 0.4 mM-3 mM dATP, 0.2 mM-0.6 mM dCTP, 0.2 mM-0.6 mM dTTP, 0.1 mM-0.4 mM dGTP, 1.5 mM-2.5 mM ATP; ionic strength and pH modifying agents: 100 mM-105 mM Tris-HCl, pH 8.0-8.8; monovalent metal hydrochloric acid salts, e.g., NaCl, KCl, LiCl ranging from 20 mM to 50 mM; and stabilizers and cryoprotectants: 15 mM-30 mM DTT; 0.1%-0.4% Triton X-100; 10%-20% (v/v) glycerol; 0.05%-0.15% NP 40; 0.05%-0.15% Tween 20; and 0.02 mM-0.1 mM EDTA.

In one embodiment the disclosed composition comprises enzymes: 1 u/µl T4 polynucleotide kinase, 0.32 u/µl T4 DNA polymerase, 0.12 u/µl Klenow fragment, and 0.2 u/µl mod-Tbr DNA polymerase; reaction co-factors and nucleotides: 20 mM $MgCl_2$, 2 mM dATP, 0.4 mM dCTP, 0.4 mM dTTP, 0.2 mM dGTP, 2 mM ATP; ionic strength and pH modifying agents: 100-105 mM Tris-HCl, pH 8.3; monovalent metal hydrochloric acid salts e.g. NaCl, KCl, LiCl ranging from 20 mM to 50 mM; and stabilizers and cryoprotectants: 20 mM DTT; 0.2% Triton X-100; 12% (v/v) glycerol; 0.07% NP 40; 0.07% Tween 20; and 0.024 mM EDTA.

The invention will now be described in further detail by way of illustration only with reference to the following examples.

EXAMPLE 1

Demonstration that Different Enzymes Require Different Buffers

It is known in the art that optimal storage and reaction conditions are distinctive to each enzyme. Enzyme storage conditions often differ from recommended reaction conditions as shown in Table 2 showing components of storage and reaction buffers of DNA blunting, phosphorylation and dA-tailing enzymes sold by the following commercial suppliers: Thermo Fisher Scientific, New England Biolabs and Life Technologies.

TABLE 2

Storage buffers (SB) and reaction buffers (RB) of enzymes used for blunting, phosphorylation, and dA-tailing of DNA fragments

|  |  | Thermo Fischer Scientific | | New England Biolabs | | Life Technologies | |
| --- | --- | --- | --- | --- | --- | --- | --- |
|  |  | SBx1 | RBx1 | SBx1 | RBx1 | SBx2 | RBx1 |
| T4 DNA Polymerase | Salts | 200 mM KCl | 6.6 mM $MgCl_2$ 16.8 mM $(NH_4)_2SO_4$ | — | 10 mM $MgCl_2$ 50 mM NaCl | — | 50 mM Mg acetate 66 mM Na acetate |
|  | Buffer | 20 mM $KPO_4$ | 67 mM Tris-HCl | 100 mM $KPO_4$ | 10 mM Tris-HCl | 100 mM $KPO_4$ | 33 mM Tris-acetate |
|  | pH (25° C.) | 7.5 | 8.8 | 6.5 | 7.9 | 6.5 | 7.9 |
|  | Detergents | — | — | — | — | — | — |
|  | Glycerol | 50% (v/V) | — | 50% (v/v) | — | 50% (v/v) | — |
|  | Additives | 2 mM DTT | 1 mM DTT | 1 mM DTT | 2 mM DTT | 10 mM 2-mercaptoethanol | 1 mM DTT |
| Klenow Fragment | Salts | — | 5 mM $MgCl_2$ | — | 50 mM NaCl 10 mM $MgCl_2$ | — | 50 mM NaCl 10 mM $MgCl_2$ |
|  | Buffer | 25 mM Tris-HCl | 50 mM Tris-HCl | 25 mM Tris-HCl | 10 mM Tris-HCl | — | 50 mM Tris-HCl |
|  | pH (25° C.) | 7.5 | 8.0 | 7.4 | pH 7.9 | — | 8.0 |
|  | Detergents | — | — | — | — | — | — |
|  | Glycerol | 50% (v/V) | — | 50% (v/v) | — | — | — |
|  | Additives | 1 mM DTT 0.1 mM EDTA | 1 mM DTT | 1 mM DTT 0.1 mM EDTA | 1 mM DTT | — | — |

TABLE 2-continued

Storage buffers (SB) and reaction buffers (RB) of enzymes used for blunting, phosphorylation, and dA-tailing of DNA fragments

| | | Thermo Fischer Scientific | | New England Biolabs | | Life Technologies | |
|---|---|---|---|---|---|---|---|
| | | SBx1 | RBx1 | SBx1 | RBx1 | SBx2 | RBx1 |
| T4 DNA Polynucleotide Kinase | Salts | 25 mM KCl | 10 mM MgCl$_2$ | 50 mM CKl | 10 mM MgCl$_2$ | 25 mM KCl | 10 mM MgCl 100 mM KCl |
| | Buffer | 20 mM Tris-HCl | 50 mM Tris-HCl | 10 mM Tris-HCl | 70 mM Tris-HCl | 50 mM Tris-HCl | 70 mM Tris-HCl |
| | pH (25° C.) | 7.5 | 7.68 | 7.45 | 7.6 | 7.6 | 7.6 |
| | Detergents | — | — | — | — | — | — |
| | Glycerol | 50% (v/V) | — | 50% (v/V) | — | 50% (v/v) | — |
| | Additives | 2 mM DTT 0.1 mM EDTA | 5 mM DTT 0.1 mM spermidine | 1 mM DTT 0.1 mM EDTA 0.1 pM ATP | 5 mM DTT | 5 mM DTT 0.1 pM ATP 0./2 mg/ml BSA | 1 mM 2-mercaptoethanol |
| Taq DNA polymerase, recombinant | Salts | 100 mM KCl | 50 mM KCl MgCl$_2$* dNTPs* | 100 mM KCl | 50 mM KCl 1.5 mM MgCl$_2$ dNTPS* | — | 50 mM KCl MgCl$_2$ dNTPs* |
| | Buffer | 20 mM Tris-HCl | 10 mM Tris-HCl | 10 mM Tris-HCl | 10 mM Tris-HCl | 20 mM Tris-HCl | 20 mM Tris-HCl |
| | pH (25° C.) | 8.0 | 8.8 | 7.4 | 8.3 | 8.0 | 8.4 |
| | Detergents | 0.5% Tween 20 0.5% Nonidet P4) | 0.08%$ Nonidet P4O | 0.5% Tween 20 0.5% IGEPAL CA-630 | — | — | — |
| | Glycerol | 50% (v/V) | — | 50% (v/v) | — | 50% (v/v) | — |
| | Additives | 1 mM DTT 0.1 mM EDTA | — | 1 mM DTT 0.1 mM EDTA | — | 0.1 mM EDTA 1 mM DTT Stabilizers | — |

To arrive at the inventive composition, all the above indicated enzymes T4 DNA polymerase, Klenow fragment, T4 DNA polynucleotide kinase and modified thermophilic polymerase having end-tailing activity, such as modified *Thermus brockianus* or *Thermus aquaticus* DNA polymerases, have to be premixed into a stable blend capable of efficient blunting, phosphorylation, and dA-tailing of a DNA fragment in a single step, and in one container. It is important to note that this is far from trivial, and even those skilled in the art would need to test a large number of storage and reaction conditions to obtain a mixture that would be stable when stored, and efficient when used in the enzymatic reaction, and there would be with no guarantee to determine the optimal storage and reaction conditions. Enzymes in such a mixture may have different optimal requirements, making them incompatible in a single blend. Moreover, in preparation of ready-to-use 1×-2× enzyme mixtures, the use of highly concentrated cryoprotectants such as glycerol is often inappropriate due to their negative impact on enzymatic reactions as they affect physical and chemical environment resulting in changed reaction conditions. Also, high concentrations of cryoprotectants may have inhibitory effect on enzyme activity. As a result, only low concentrations of cryoprotectants may be used, which are often insufficient to prevent freezing of enzymes blends. Therefore, there is a very high risk of enzyme activity loss in multiple freezing-thawing cycles. Additives required for one enzyme may be detrimental either for storage and/or for catalytic activity of another enzyme of the component blend. The same is true for salts, as well as their concentration, used for buffering systems, and for pH in the ready-to-use mixture. In general, stability of a ready-to-use mixture is determined by the monovalent salt tolerance and the presence of sufficient ionic strength. The monovalent salt may by any salt in which the metal, e.g., Na, K, or Li, has a net 1$^+$ charge in solution.

In preparing stable enzyme master mix for DNA fragment end repair/dA tailing, in contrast to the previously disclosed information in this Example, the disclosed ready-to-use composition comprising the enzymes T4 DNA polymerase, Klenow fragment, T4 polynucleotide kinase, and mod-Tbr or mod-Taq DNA polymerases, and all other necessary reaction components previously described, enables efficient one tube blunting, phosphorylation and dA-tailing of DNA fragments, which results in the yield of dATP-extended DNA fragments exceeding 75%. The disclosed composition provides a master mixture that reduces the number of pipetting steps required for preparation of DNA fragments, such as for NGS library preparation, when compared with other commercial NGS sample preparation kits. Reducing pipetting steps simplifies NGS library preparation workflow because it involves less manipulations and hands-on time, minimizes errors, and thus provides more consistent results across sample sets. The disclosed composition mixture modifies DNA fragments in much shorter reaction times, as it blunts and phosphorylates DNA fragments in five minutes at 20° C., and modifies these fragments by adding dATP at their 3' ends in ten minutes at 72° C. Thus, using the disclosed composition mixture, both reactions collectively take only fifteen minutes.

One embodiment of the disclosed composition, referred to as the End Conversion Master Mix, was tested. The End Conversion Master Mix comprised enzymes, buffers and other necessary reaction/storage components in the following 2× concentrations and ratios: 1 u/µl T4 polynucleotide kinase; 0.32 u/µl T4 DNA polymerase; 0.12 u/µl Klenow fragment, and 0.2 u/µl mod-Tbr DNA polymerase. Reaction co-factors and nucleotides were: 20 mM MgCl$_2$, 2 mM dATP; 0.4 mM dCTP; 0.4 mM dTTP; 0.2 mM dGTP; 2 mM ATP. Ionic strength and pH of the End Conversion Master Mix may be formulated using 100 mM-105 mM Tris-HCl, pH 8.3 and monovalent metal hydrochloric acid salts, e.g. NaCl, KCl, LiCl, at 20 mM to 50 mM. Stabilizers and cryoprotectants were: 20 mM DTT; 0.2% Triton X-100; 12% (v/v) glycerol; 0.07% NP 40; 0.07% Tween 20; and 0.024 mM EDTA.

Other salts and stabilizers suitable for use in enzyme blends will be apparent to those skilled in the art and may differ for different DNA polymerases used in blunting and/or dA-tailing reactions.

EXAMPLE 2

Effect of Buffers and Polymerase Compositions on Blunting, Tailing, and Phosphorylation To test DNA fragment 3' end tailing efficiency and analyze the potential bias depending on the 3' terminal nucleotide, a model system of four oligoduplexes differing in both length and 3' terminal nucleotide and labeled with Cy5 at their 5' ends was developed and used (FIG. 1).

The dA-tailing ability of Klenow fragment exo⁻ mutant was examined and shown in FIG. 2, where lane (A) is an optimal Klenow fragment buffer (10× Reaction buffer, EP0421) supplemented with 0.2 mM dATP; lane (B) is commercial buffer G with 1 mM DTT and 0.2 mM dATP; and lane (C) is optimized DNA end repair buffer (Fast DNA End repair kit K0771) dA-tailing reactions were performed at 37° C. using five units of enzyme in 50 µl reaction mixture containing 7.5 pmol equimolar mixture of Cy-5 labeled oligoduplexes shown in FIG. 1. The band pairs represent the oligoduplex with and without a single additional dA.

FIG. 2 shows lane A—1× Klenow buffer+0.2 mM dATP; lane B—1×G buffer with 1 mM DTT+0.2 mM dATP; and lane C—1× end repair buffer.

Results presented in FIG. 2 suggested that Klenow fragment exo⁻, even after 30 minutes of incubation, in all three tested reaction mixtures was unable to extend oligonucleotides uniformly, extending 3'-terminal pyrimidines (C/T) more efficiently compared to those featuring 3'-terminal purines (A/G). In addition, dA-tailing by Klenow fragment exo⁻ was least efficient in (C) buffer which was optimal for enzymes performing blunting and phosphorylation of DNA fragments, but was suboptimal for Klenow fragment.

Figure 3:
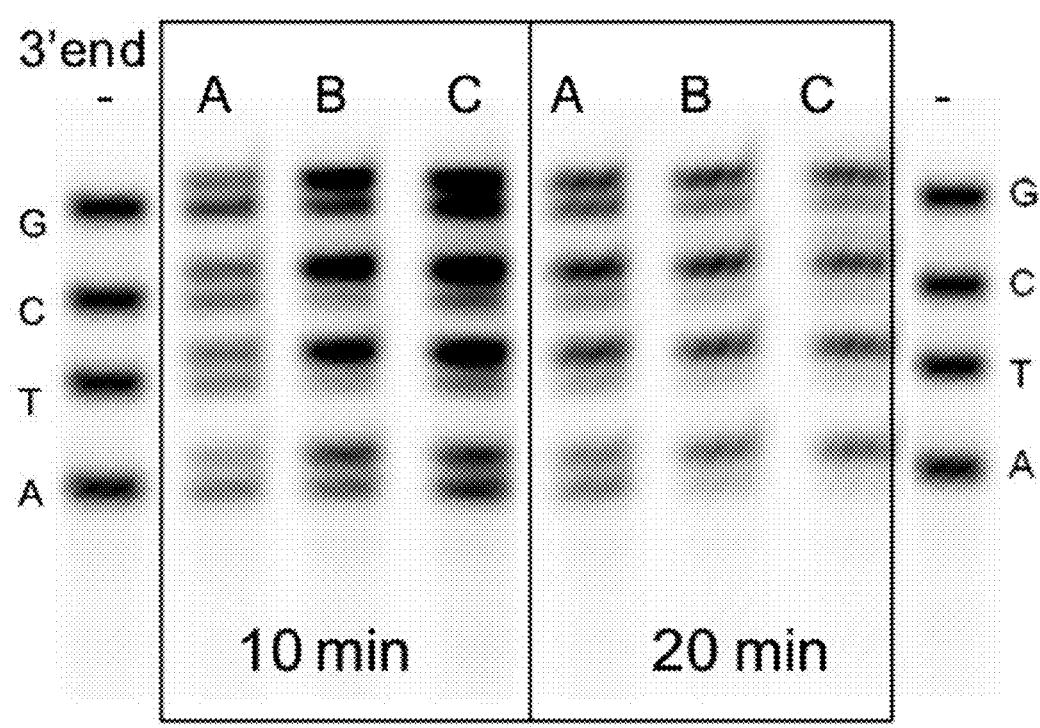
FIG. 3 shows separated duplex oligos of FIG. 1 treated with Taq DNA polymerase in various reaction buffers at various pH showing dA tailing efficiency.

The dA-tailing ability of Taq DNA polymerase was examined and shown in FIG. 3, where lane (A) is an optimized DNA end repair buffer pH 7.5; lane (B) is the same as in A but pH 8.0; and lane (C) the same as in A but pH 8.3 Optimized buffer is 10× End Repair Reaction Mix from Fast DNA End Repair kit K0771. Reactions were performed at 60° C. using 7.5 units enzyme in 50 µl reaction mixture containing 7.5 pmol equimolar mixture of Cy-5 labeled oligoduplexes shown in FIG. 1.

FIG. 3A—1× end repair buffer, pH 7.5; B—1× end repair buffer, pH 8.0; C—1× end repair buffer, pH 8.3.

Results presented in FIG. 3 suggested that Taq DNA polymerase preferred extension of 3'-terminal pyrimidines at pH 7.5, which is optimal for blunting and phosphorylation reactions. A increased pH from pH 7.5 to pH 8.3 had a positive effect on Taq DNA polymerase dA-tailing efficiency and uniformity. However, even after 20 minutes of incubation, the oligonucleotide with the 3' terminal G was extended less efficiently compared to other substrates used in this experiment.

Optimization of reaction conditions experiments with mod-Tbr DNA polymerase (exo-) revealed that the enzyme preferred increased pH for dA-tailing like Taq polymerase, but showed less preference for DNA fragments possessing 3' terminal C or T (see FIG. 4) To ensure better dA-tailing efficiency, the reaction mixture was enriched with dATP, increasing its concentration to 1 mM. To mimic the situation when various amounts of DNA fragments have to be blunted and dA-tailed, the experiment was conducted with constant amounts (5 units) of mod-Tbr DNA polymerase in the optimized buffer (10× End Repair Reaction Mix from Fast DNA End Repair kit K0771) at pH 8.3 using increased dATP concentration (1 mM) and varying amounts of oligoduplexes shown in FIG. 1.

Figure 4:
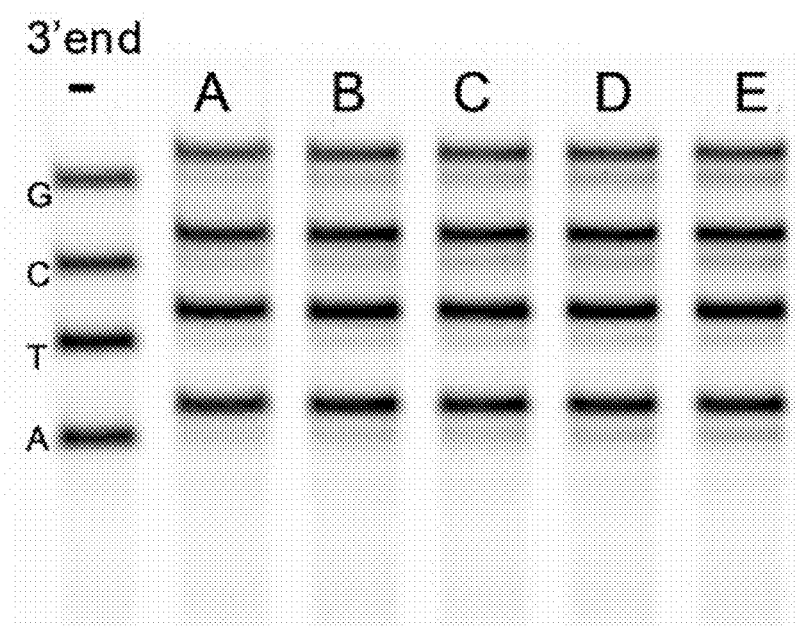
FIG. 4 shows separated duplex oligos of FIG. 1 treated with modified *Thermus brockianus* DNA polymerase with various substrate concentrations showing dA-tailing efficiency.

FIG. 4 shows lane A 1.5 pmol mixture of the double-stranded oligonucleotides; lane B 7.5 pmol mixture of the double-stranded oligonucleotides; lane C 15 pmol mixture of the double-stranded oligonucleotides; lane D 22.5 pmol mixture of the double-stranded oligonucleotides; and lane E 30 pmol mixture of the double-stranded oligonucleotides. Reactions were performed at 60° C. in 50 µl of reaction mixture for ten minutes.

Results presented in FIG. 4 show that mod-Tbr DNA polymerase extends efficiently and uniformly all types of DNA ends in a broad range of concentrations of substrates tested, thus outperforming Klenow fragment exo⁻ and Taq DNA polymerase enzymes.

A control DNA fragment was used to test both DNA end repair and the DNA 3' end tailing efficiency in one reaction mixture. The DNA fragment was 265 bp having 3' and 5' terminal protruding ends and lacking phosphates at its 5' ends, and was generated by PsuI and PstI cleavage and subsequent treatment with alkaline phosphatase. This DNA substrate mimics the situation after physical shearing of DNA when individual DNA fragments may contain 3' and/or 5' protruding ends and lack 5' terminal phosphates.

Figure 5:
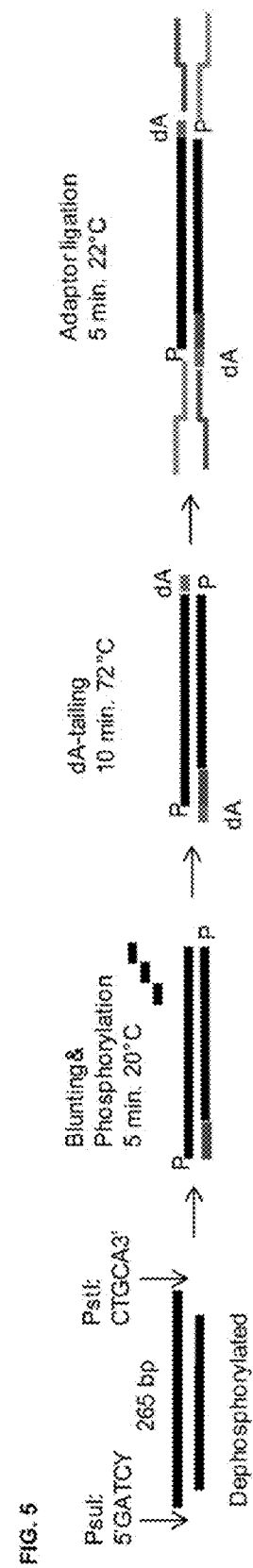
FIG. 5 schematically illustrates DNA end repair and 3' terminal extension in one reaction mixture according to one embodiment.
Figure 6:
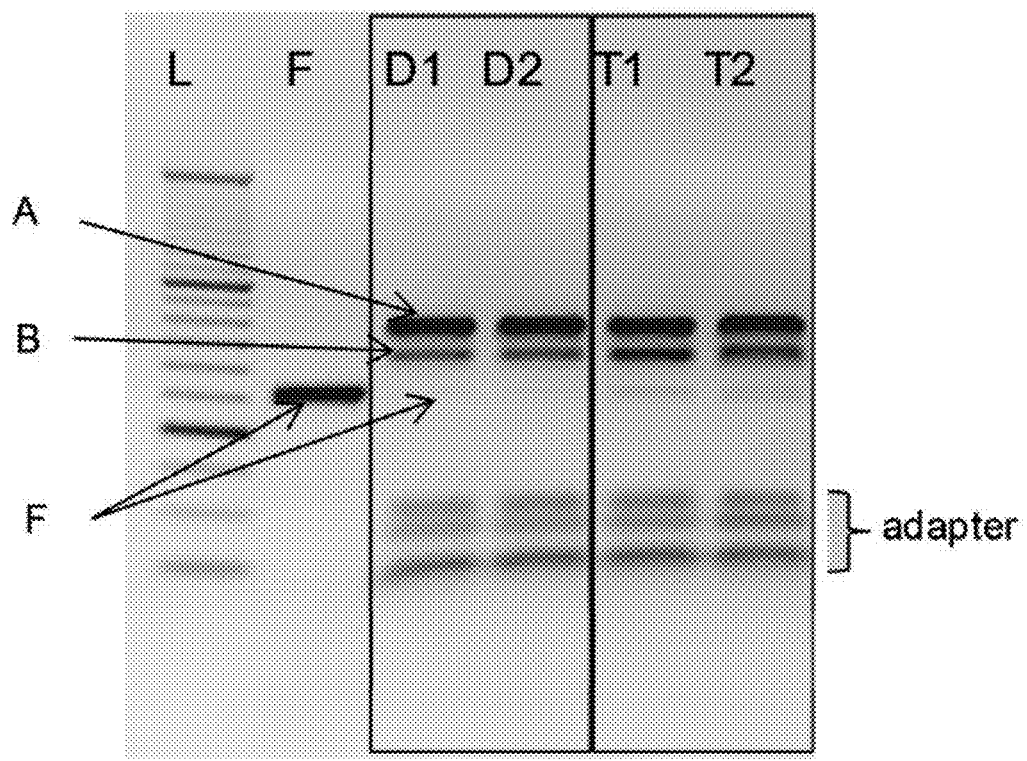
FIG. 6 shows DNA end repair and 3' terminal extension in one reaction mixture using different polymerases.

One µg of DNA fragment was incubated in 50 µl of a reaction mixture with commercial End Repair Enzyme Mix (Thermo Scientific, K0771) and 5 units of a thermophilic DNA polymerase: mod-Tbr DNA polymerase or Taq DNA polymerase. Reaction mixtures were incubated for five minutes at 20° C., allowing the end repair enzymes to blunt and phosphorylate DNA fragment ends, followed by incubation for ten minutes at 72° C., a condition favorable for simultaneous inactivation of mesophylic end repair enzymes and DNA 3' end tailing by the thermophilic DNA polymerase. After this step, a DNA adapter of 60 bp in length, and carrying a 3' terminal dT extension, was added to a final concentration of 1 µM to the reaction mixture. Ligation of the DNA adaptor to the DNA fragment was accomplished using T4 DNA ligase for five minutes at 22° C., and resulting reaction products were analyzed on a 1% agarose gel. The experimental scheme is shown in FIG. 5. The results are shown in FIG. 6, where D1 and D2 are samples prepared using mod-Tbr DNA polymerase; T1 and T2 are samples prepared using Taq DNA polymerase; F represents the control DNA fragment; L is O'RangeRuler 50 bp DNA Ladder (Thermo Scientific, SM0613); A is the 381 bp reaction product with adapters ligated to both DNA fragment ends (60+261+60 bp); and B is the 321 bp reaction product with adapter ligated to one DNA fragment end (261+60 bp).

FIG. 6 shows lanes D1, D2—samples prepared using DyNAmolV DNA polymerase; lanes T1, T2—samples prepared using Taq DNA polymerase; F—control DNA fragment; A shows 381 bp reaction product with adapters ligated to both DNA fragment ends (60+261+60 bp); B shows 321 bp reaction product with adapter ligated to one DNA fragment end (261+60 bp); L—O'RangeRuler 50 bp DNA Ladder (Thermo Scientific, SM0613).

Results presented in FIG. 6 show that mod-Tbr DNA polymerase generated more products of the correct structure (fragment A), indicating that this enzyme outperformed Taq DNA polymerase and was more appropriate for use with DNA end repair enzymes in one reaction mixture. Only blunted and then dA-tailed control DNA fragment can be ligated to dT-containing adapters. The dominating largest band A represents DNA fragments with adapters ligated to both ends, while only a small fraction of control DNA fragment F was left unprocessed.

These data demonstrated that the efficiency of DNA end repair and DNA 3' end dA-tailing reactions differ when performed in single reaction mixture using different thermostable DNA polymerases, and further, that a reaction mixture of present invention comprising mod-Tbr outperforms in efficiency other compositions previously used for said reactions. Also, it is noteworthy that when an inventive composition was used, there were no traces of larger DNA fragments which could appear with incomplete dA-tailing of blunted DNA fragments which are then ligated together.

EXAMPLE 3

Stability of 2× Concentrated End Conversion Master Mix

Figure 7:
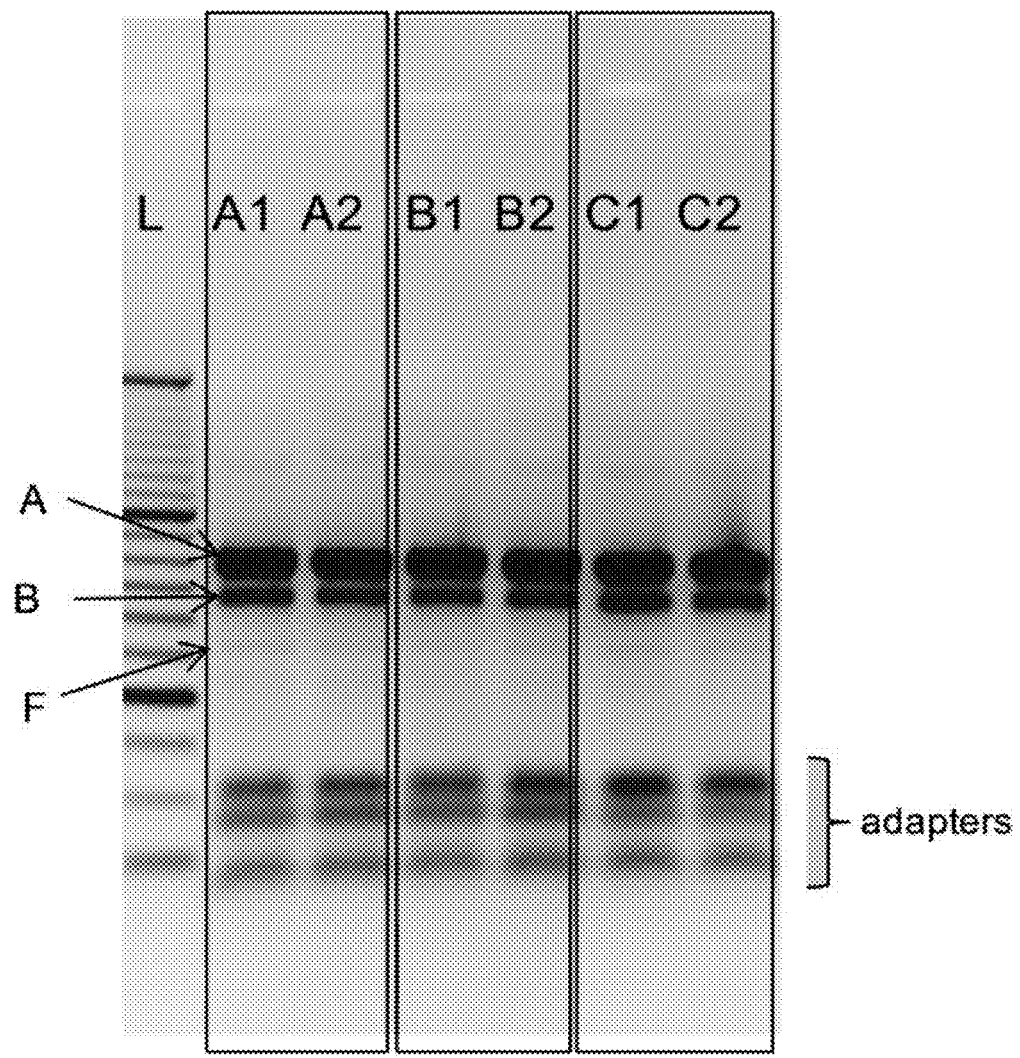
FIG. 7 shows stability of the described composition according to one embodiment.

For stability testing, a 2× End Conversion Master Mix as disclosed was stored at −20° C. and +25° C., to represent accelerated stability testing, for different periods of time. The stability test was performed using the same experimental scheme shown in FIG. 5. One µg of control DNA fragment was incubated for five min in 50 µl reaction mixture of 1× End Conversion Master Mix that had been stored at −20° C., allowing the DNA end repair enzymes to blunt and phosphorylate DNA ends, followed by incubation for ten minutes at 72° C., a condition favorable for simultaneous inactivation of mesophylic DNA end repair enzymes and DNA 3' end tailing by mod-Tbr DNA polymerase. After this step, a DNA adapter of 60 bp in length carrying 3' terminal dT extension was added to a final 1 µM concentration to the reaction mixture, and ligation for five min at 22° C. using T4 DNA ligase was performed. The resulting reaction products were analyzed on a 1% agarose gel. The results are shown in FIG. 7, where A1 and A2 are samples prepared using End Conversion Master Mix stored 2 weeks at −20° C.; B1 and B2 are samples prepared using End Conversion Master Mix stored 1 week at +25° C.; C1 and C2 are samples prepared using End Conversion Master Mix stored 2 weeks at +25° C.; F is the control DNA fragment; L is O'RangeRuler 50 bp DNA Ladder (Thermo Scientific, SM0613); A is the 381 bp reaction product with adapters ligated to both DNA fragment ends (60+261+60 bp); and B is the 321 bp reaction product with adapter ligated to one DNA fragment end (261+60 bp).

FIG. 7 shows A1, A2—samples prepared using End Conversion Master Mix, stored 2 weeks at −20° C.; B1, B2—samples prepared using End Conversion Master Mix, stored 1 week at +25° C.; C1, C2-samples prepared using End Conversion Master Mix, stored 2 weeks at +25° C.; F—control DNA fragment; A—381 bp reaction product with adapters ligated to both DNA ends (60+261+60 bp); B—321 bp reaction product with adapter ligated to one DNA end (261+60 bp); L—O'RangeRuler 50 bp DNA Ladder (Thermo Scientific, SM0613).

Results presented in FIG. 7 indicated that End Conversion Master Mix retained functional activity for two weeks at +25° C., thus is considered to be stable during prolonged storage times. The composition was stable for at least one week at 4° C. In addition, the results presented in FIG. 7 indicated that End Conversion Master Mix provided efficient blunting, phosphorylation, and dA tailing in a single mixture.

Applicants incorporate by reference the material contained in the accompanying computer readable Sequence Listing identified as Thermo_Fisher_Scientific_Baltics_UAB_33_ST25.txt, having a file creation date of Sep. 24, 2013 12:29 P.M. and file size of 2.06 kilobytes.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. An enzyme composition comprising in a single container a buffer comprising nucleoside triphosphates and a plurality of enzymes separately capable of blunting, phosphorylating and adenylating DNA fragments, with the enzyme capable of adenylating DNA being a chimeric DNA polymerase comprising a thermophilic DNA polymerase fused to a non-specific DNA-binding domain, wherein the thermophilic DNA polymerase lacks 5'-3' and 3'-5' exonuclease activity, and with the enzymes capable of blunting and phosphorylating DNA fragments being selected from the group consisting of T4 DNA polymerase, T7 DNA polymerase, Klenow fragment, and T4 polynucleotide kinase, and the composition being stable for at least one week at 4° C.

2. The composition of claim 1 where the chimeric DNA polymerase is a *Thermus* species thermophilic DNA polymerase fused to non-specific DNA-binding domain.

3. The composition of claim 2 where the chimeric DNA polymerase is a *Thermus* species polymerase fused to non-specific DNA-binding domain from *Sulfolobus* family.

4. The composition of claim 1 where the nucleoside triphosphates are dATP, dCTP, dTTP, and dGTP, where the concentration of dATP ranges from 0.4 to 3 mM, the concentration of dCTP ranges from 0.2 to 0.6 mM, the concentration of dTTP ranges from 0.2 to 0.6 mM, and the concentration of dGTP ranges from 0.1 to 0.4 mM.

5. The composition of claim 1 where the concentration of dATP is about 2 mM, the concentration of dCTP is about 0.4 mM, the concentration of dTTP is about 0.4 mM, and the concentration of dGTP is about 0.2 mM.

6. The composition of claim 1 where the buffer further comprises at least one component selected from the group consisting of Tris-HCl, $MgCl_2$, DTT, a monovalent metal hydrochloric acid salt selected from NaCl, KCl, and LiCl, ATP, Triton X-100, glycerol, NP 40, EDTA, and Tween 20.

7. The composition of claim 5 where, when present, the concentration of Tris-HCl ranges from 100 mM to 105 mM inclusive at a pH of 8.0 to 8.8; the concentration of $MgCl_2$ ranges from 15 to 25 mM inclusive, the concentration of DTT ranges from 15 to 30 mM inclusive, the concentration of monovalent metal hydrochloric acid salt ranges from 20 mM to 50 mM inclusive, the concentration of ATP ranges from 1.5 to 2.5 mM inclusive, the concentration of Triton X-100 ranges from 0.1 to 0.4% inclusive, the concentration of glycerol ranges from 10 to 20% inclusive, the concentration of NP 40 ranges from 0.05 to 0.15% inclusive, the concentration of EDTA ranges from 0.02 to 0.1 mM inclusive, and the concentration of Tween 20 ranges from 0.05 to 0.15% inclusive.

8. The composition of claim 1 where the concentration of T4 DNA polymerase ranges from 0.2 to 0.5 U/µl inclusive, the concentration of Klenow fragment ranges from 0.1 to 0.2 U/µl inclusive, and the concentration of T4 polynucleotide kinase ranges from 0.5 U/µl to 1.5 U/µl inclusive.

9. The composition of claim 8 where the concentration of T4 DNA polymerase is about 0.32 U/µl, the concentration of Klenow fragment is about 0.12 U/µl, and the concentration of T4 polynucleotide kinase is about 1 U/µl.

10. The composition of claim 1 where the concentration of the thermophilic DNA polymerase ranges from 0.1 to 0.5 U/µl inclusive.

11. The composition of claim 1 where the concentration of the thermophilic DNA polymerase is about 0.2 U/µl.

12. An enzyme composition comprising in a single container Tris-HCl, $MgCl_2$, DTT, KCl, dATP, dCTP, dTTP, dGTP, ATP, Triton X-100, glycerol, NP 40, EDTA, Tween 20, T4 polynucleotide kinase, T4 DNA polymerase, Klenow fragment, and chimeric thermophilic DNA polymerase from *Thermus brockianus* or *Thermus* sp. fused to DNA-binding domain from *Sulfolobus* family, the composition contained in a single container and being storage stable.

13. The composition of claim 12 where the concentration of dATP is at least five times the concentration of each of dCTP, dTTP, and dGTP.

* * * * *

SEQUENCE LISTING

```
<160> NUMBER OF SEQ ID NOS: 8

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(1)
<223> OTHER INFORMATION: 5' Cy5 label

<400> SEQUENCE: 1
tgcagacatg ggtaggcatc cttggcgtag ttaccaag                              38

<210> SEQ ID NO 2
<211> LENGTH: 38
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 2
acgtctgtac ccatccgtag gaaccgcatc aatggttc                              38

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(1)
<223> OTHER INFORMATION: 5' Cy5 label

<400> SEQUENCE: 3
tgcagacatg ggtaggcatc cttggcgtag ttacc                                 35

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acgtctgtac ccatccgtag gaaccgcatc aatgg                                 35

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(1)
<223> OTHER INFORMATION: 5' Cy5 label

<400> SEQUENCE: 5
tgcagacatg ggtaggcatc cttggcgtag tt                                    32

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acgtctgtac ccatccgtag gaaccgcatc aa                                    32

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(1)
```

```
<223> OTHER INFORMATION: 5' Cy5 label

<400> SEQUENCE: 7
tgcagacatg ggtaggcatc cttggcgta                                29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acgtctgtac ccatccgtag gaaccgcat                                29
```